US00PP33370P2

(12) United States Plant Patent
Kobayashi

(10) Patent No.: US PP33,370 P2
(45) Date of Patent: Aug. 17, 2021

(54) POINSETTIA PLANT NAMED 'DOPOINFRO'

(50) Latin Name: ***Euphorbia pulcherrima* Willd.**
Varietal Denomination: Dopoinfro

(71) Applicant: DUMMEN GROUP B.V., De Lier (NL)

(72) Inventor: Ruth Kobayashi, Carlsbad, CA (US)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/873,883

(22) Filed: Aug. 4, 2020

(51) Int. Cl.
*A01H 5/00* (2018.01)
*A01H 6/38* (2018.01)

(52) U.S. Cl.
USPC ..... Plt./304

(58) Field of Classification Search
USPC ..... Plt./304
CPC ... A01H 5/02; A01H 5/00; A01H 5/12; A01H 6/38; A01H 6/385
See application file for complete search history.

(56) References Cited

PUBLICATIONS

Floral Daily. Plantpeddler Poinsettia Variety Day 2019 results, retrieved on Jan. 28, 2021, retrieved from the Internet at https://www.floraldaily.com/article/9171482/plantpeddler-poinsettia-variety-day-2019-results/, 6 pp. (Year: 2019).*

* cited by examiner

*Primary Examiner* — June Hwu
(74) *Attorney, Agent, or Firm* — C. Anne Whealy

(57) ABSTRACT

A new and distinct cultivar of Poinsettia plant named 'Dopoinfro', characterized by its uniform, upright and mounded plant habit; moderately vigorous growth habit; freely and upright branching habit; dark green-colored leaves; plants flower on or about November 16 in Southern California under natural season conditions; large inflorescences with bright white-colored flower bracts; and good post-production longevity.

1 Drawing Sheet

Botanical designation: *Euphorbia pulcherrima* Willd.
Cultivar denomination: 'DOPOINFRO'.

STATEMENT REGARDING PRIOR DISCLOSURES BY THE INVENTOR AND APPLICANT

The Inventor and Applicant assert that no sales, publications or advertisements relating to sales, offers for sale or public distribution occurred more than one year prior to the effective filing date of this application. Any information about the claimed plant would have been obtained from a direct or indirect disclosure from the Inventor and/or the Applicant. Inventor and Applicant claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of Poinsettia plant, botanically known as *Euphorbia pulcherrima* Willd., and hereinafter referred to by the cultivar name 'Dopoinfro'.

The new Poinsettia plant is a product of a planned breeding program conducted by the Inventor in Encinitas, Calif. The objective of the breeding program is to create new uniform Poinsettia plants having large inflorescences with attractive flower bracts and excellent post-production longevity.

The new Poinsettia plant is a naturally-occurring whole plant mutation of a proprietary selection of *Euphorbia pulcherrima* Willd. identified as code number EZ13-000123-083-X001, not patented. The new Poinsettia plant was discovered and selected by the Inventor as a single flowering plant from within a population of plants of the mutation parent selection in a controlled greenhouse environment in Encinitas, Calif. on Nov. 24, 2017.

Asexual reproduction of the new Poinsettia plant by terminal vegetative cuttings in a controlled greenhouse environment in Encinitas, Calif. since January, 2018 has shown that the unique features of this new Poinsettia plant are stable and reproduced true to type in successive generations of asexual reproduction.

SUMMARY OF THE INVENTION

Plants of the new Poinsettia have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Dopoinfro'. These characteristics in combination distinguish 'Dopoinfro' as a new and distinct Poinsettia plant:

1. Uniform, upright and mounded plant habit.
2. Moderately vigorous growth habit.
3. Freely and upright branching habit.
4. Dark green-colored leaves.

5. Under natural season conditions, plants flower on or about November 16 in Southern California.
6. Large inflorescences with bright white-colored flower bracts.
7. Good post-production longevity.

In side-by-side comparisons conducted in Encinitas, Calif., plants of the new Poinsettia differ primarily from plants of the mutation parent selection in time to flower as plants of the new Poinsettia flower about eleven days earlier than plants of the mutation parent selection when grown under natural season conditions.

Plants of the new Poinsettia can be compared to plants of the *Euphorbia pulcherrima* Willd. 'PER10606', disclosed in U.S. Plant Pat. No. 20,351. In side-by-side comparisons, plants of the new Poinsettia differ primarily from plants of 'PER10606' in the following characteristics:

1. Leaves of plants of the new Poinsettia are lighter green in color than leaves of plants of 'PER10606'.
2. Plants of the new Poinsettia flower about nine days later than plants of 'PER10606' when grown under natural season conditions.
3. Plants of the new Poinsettia have bright white-colored flower bracts whereas plants of 'PER10606' have creamy white-colored flower bracts.

Plants of the new Poinsettia can also be compared to plants of the *Euphorbia pulcherrima* Willd. 'Peterstar White', disclosed in U.S. Plant Pat. No. 9,878. In side-by-side comparisons, plants of the new Poinsettia differ primarily from plants of 'Peterstar White' in the following characteristics:

1. Branching habit of plants of the new Poinsettia is more upright than branching habit of plants of 'Peterstar White'.
2. Plants of the new Poinsettia flower about eleven days earlier than plants of 'Peterstar White' when grown under natural season conditions in Southern California.
3. Plants of the new Poinsettia have bright white-colored flower bracts whereas plants of 'Peterstar White' have lemony white-colored flower bracts.

BRIEF DESCRIPTION OF THE PHOTOGRAPH

The accompanying photograph illustrates the overall appearance of the new Poinsettia plant showing the colors as true as it is reasonably possible to obtain in colored reproductions of this type. Colors in the photograph may differ slightly from the color values cited in the detailed botanical description which accurately describe the colors of the new Poinsettia plant.

The photograph is a side perspective view of a typical flowering plant of 'Dopoinfro' grown in a container.

DETAILED BOTANICAL DESCRIPTION

Plants used in the aforementioned photograph and in the following detailed description were grown during the summer to late autumn in 16.5-cm containers in a polyethylene-covered greenhouse in Encinitas, Calif. under natural season conditions and cultural practices typical of commercial Poinsettia production. During the production of the plants, day temperatures averaged 24° C., night temperatures averaged 14° C. and light levels ranging from 3,500 to 4,500 foot-candles. Plants were pinched one time about four weeks after sticking rooted cuttings and were 23 weeks old when the photographs and the description were taken. Measurements and numerical values represent averages for typical flowering plants. In the following description, color references are made to The Royal Horticultural Society Colour Chart, 2015 Edition, except where general terms of ordinary dictionary significance are used.

Botanical classification: *Euphorbia pulcherrima* Willd. 'Dopoinfro'.

Parentage: Naturally-occurring whole plant mutation of a proprietary selection of *Euphorbia pulcherrima* Willd. identified as code number EZ13-000123-083-X001, not patented.

Propagation:

*Type*.—Terminal vegetative cuttings.

*Time to initiate roots*.—About seven to ten days at night temperatures about 20° C. and day temperatures about 27° C.

*Time to produce a rooted young plant*.—About four weeks at night temperatures about 20° C. and day temperatures about 27° C.

*Root description*.—Fibrous; typically white in color, actual color of the roots is dependent on substrate composition, water quality, fertilizer type and formulation, substrate temperature and physiological age of roots.

Plant description:

*Plant and growth habit*.—Uniform, upright and mounded plant habit; inverted triangle; large inflorescences with numerous flower bracts positioned above the foliar plane; moderately vigorous growth habit.

*Plant height*.—About 33 cm.

*Plant diameter or spread*.—About 51 cm.

*Lateral branch description*.—Quantity: Freely branching habit, about six to seven lateral branches develop after pinching; upright branching habit. Length: About 24.5 cm. Diameter: About 8.5 mm. Internode length: About 1.75 cm to 2 cm. Strength: Strong. Aspect: About 30° from vertical. Texture: Smooth, glabrous. Luster: Moderately glossy. Color: More green than 146A.

*Leaf description*.—Arrangement: Alternate, simple. Length: About 12.5 cm. Width: About 8.5 cm. Shape: Ovate to narrowly ovate. Apex: Acuminate. Base: Obtuse with truncate tendencies. Margin: Mostly entire to occasionally lobed; moderately undulate. Aspect: Outwardly to slightly drooping; keeled. Texture, upper and lower surfaces: Rugose, glabrous; prominent venation on lower surface. Luster, upper surface: Slightly glossy. Luster, lower surface: Matte. Venation pattern: Pinnate, arcuate. Color: Developing and fully expanded leaves, upper surface: Close to 147A; venation, close to 146A to 146B. Developing and fully expanded leaves, lower surface: Close to 147B; venation, close to 146B to 146C. Leaf petioles: Length: About 3.75 cm to 4 cm. Diameter: About 4 mm. Texture, upper and lower surfaces: Smooth, glabrous. Luster, upper and lower surfaces: Moderately glossy. Color, upper and lower surfaces: Close to 144A to 144B.

Inflorescence description:

*Inflorescence type and habit*.—Terminal inflorescences are compound corymbs of cyathia with numerous colored flower bracts subtending the cyathia; inflorescences uniformly positioned above the foliar plane.

*Fragrance*.—None detected.

*Flowering response*.—Under natural season conditions, plants typically flower on or about November 16 in Southern California; under artificial long nyctoperiod/short photoperiod conditions, plants flower about eight weeks later.

*Post-production longevity*.—Good post-production longevity; plants of the new Poinsettia maintain good substance and flower bract color for about four to six weeks under interior conditions; flower bracts persistent and cyathia not persistent.

*Inflorescence diameter*.—About 35 cm.

*Inflorescence height* (*depth*).—About 7 cm.

*Flower bracts*.—Quantity per inflorescence: Numerous, about 20 to 26. Length, largest bracts: About 17 cm. Width, largest bracts: About 9 cm. Shape: Ovate to narrowly ovate. Apex: Acuminate. Base: Obtuse with truncate tendencies. Margin: Entire to occasionally lobed; slightly undulate. Aspect: Mostly horizontal; keeled. Texture, upper and lower surfaces: Slightly rugose, glabrous; satiny; prominent venation on lower surface. Luster, upper and lower surfaces: Matte. Venation pattern: Pinnate, arcuate. Color: Developing or transitional bracts, upper surface: Ground color, more green than 137A; irregular and random sectors, close to N144A and N144B. Developing or transitional bracts, lower surface: Ground color, close to 145A; irregular and random sectors, close to 154C and 154D. Fully expanded bracts, upper and lower surfaces: Initially, close to 150D becoming closer to 155D with 155D with development. Bract petioles: Length: About 2 cm. Diameter: About 3 mm. Texture, upper and lower surfaces: Smooth, glabrous. Luster, upper and lower surfaces: Moderately glossy. Color, upper surface: Close to 144D. Color, lower surface: Close to 144C.

*Cyathia*.—Quantity per corymb: About 15 to 18. Length: About 6.5 mm. Width: About 5 mm. Shape: Ovoid. Texture: Smooth, glabrous. Color, inner and outer surfaces: Close to 144A to 144B.

*Nectaries*.—Quantity per cyathium: One. Length: About 5 mm. Width: About 4 mm. Shape: Roughly deltoid. Texture: Smooth, glabrous. Color, inner and outer surfaces: Close to 12A.

*Peduncles*.—Length: About 6 mm. Diameter: About 2 mm. Strength: Strong. Aspect: Mostly upright to slightly outwardly. Texture: Smooth, glabrous. Color: Close to 144A to 144B.

*Reproductive organs*.—Stamens: Quantity per cyathium: About 20 to 24. Filament length: About 5 mm. Filament color: Close to NN155D. Anther shape: Round to oval; bi-lobed. Anther length: Less than 1 mm. Anther color: Close to 12A. Amount of pollen: None observed. Pistils: Quantity per cyathium: One; tri-parted. Pistil length: About 7.5 mm. Stigma shape: Lanceolate, six-parted, recurved. Stigma color: Close to 154B. Style length: About 6 mm. Style color: Close to 144B to 144C. Ovary color: Close to 144B to 144C. Fruits: Quantity per cyathium: One. Length: About 1 cm. Diameter: About 8 mm. Shape: Tri-parted. Texture: Smooth, glabrous. Color: Close to 144A. Seeds: Quantity per fruit: Three, one per carpel. Length: About 4 mm. Diameter: About 4 mm. Shape: Spherical. Texture: Smooth, glabrous. Color: Close to NN155D.

Pathogen & pest resistance: To date, plants of the new Poinsettia have not been shown to be resistant to pathogens and pests common to Poinsettia plants.

Temperature tolerance: Plants of the new Poinsettia have been observed to tolerate temperatures ranging from about 16° C. to about 29° C.

It is claimed:

1. A new and distinct Poinsettia plant named 'Dopoinfro' as illustrated and described.

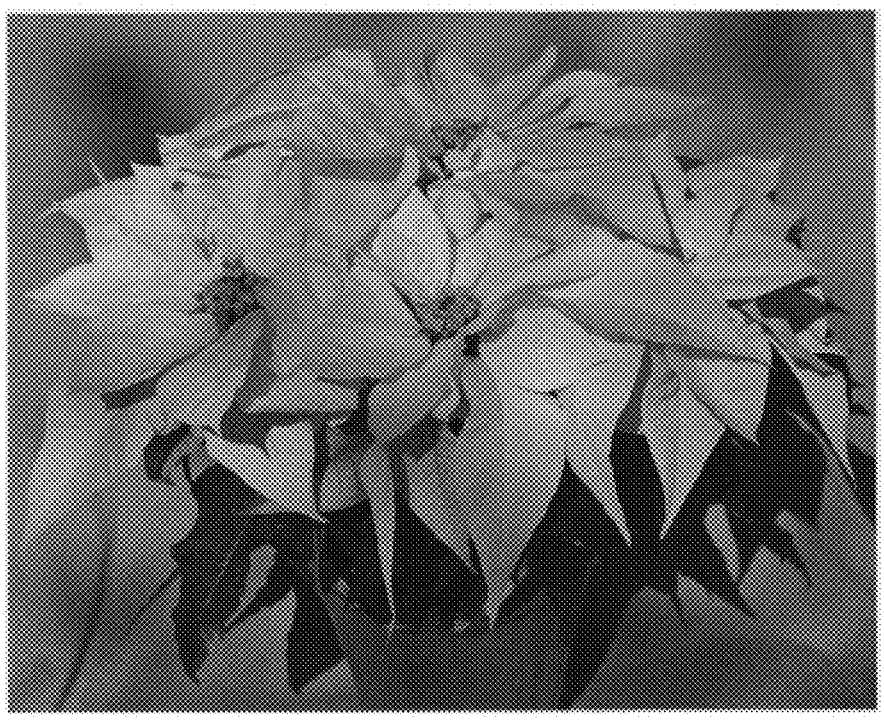

* * * * *